US00PP21722P3

(12) United States Plant Patent
Ligonnière

(10) Patent No.: US PP21,722 P3
(45) Date of Patent: Feb. 22, 2011

(54) APPLE TREE NAMED 'DALIGRIS'
(50) Latin Name: *Malus domestica Borkh*
Varietal Denomination: Daligris

(75) Inventor: Guy Ligonnière, Angers (FR)
(73) Assignee: S.N.C. Elaris, Angers (FR)

( * ) Notice: Subject to any disclaimer, the term of this patent is extended or adjusted under 35 U.S.C. 154(b) by 108 days.

(21) Appl. No.: 12/316,880

(22) Filed: Dec. 16, 2008

(65) Prior Publication Data

US 2010/0154089 P1 Jun. 17, 2010

(51) Int. Cl.
*A01H 5/00* (2006.01)

(52) U.S. Cl. ..... Plt./161

(58) Field of Classification Search ..... Plt./161
See application file for complete search history.

(56) References Cited

U.S. PATENT DOCUMENTS

PP17,672 P3 * 5/2007 Hofmann ..... Plt./161
PP18,482 P3 * 2/2008 Ligonniere ..... Plt./161
PP18,483 P3 * 2/2008 Ligonniere ..... Plt./161

* cited by examiner

*Primary Examiner*—Susan B McCormick Ewoldt
(74) *Attorney, Agent, or Firm*—Michelle Bos

(57) ABSTRACT

A new apple tree named 'Daligris' is disclosed. The fruit of the new variety is particularly notable for its eating quality and distinctive flavor and appearance. The fruit is very sweet and has a pronounced aniseed flavor, and takes on a distinctive red orange coloration as it ripens on the tree.

4 Drawing Sheets

Figure 1:
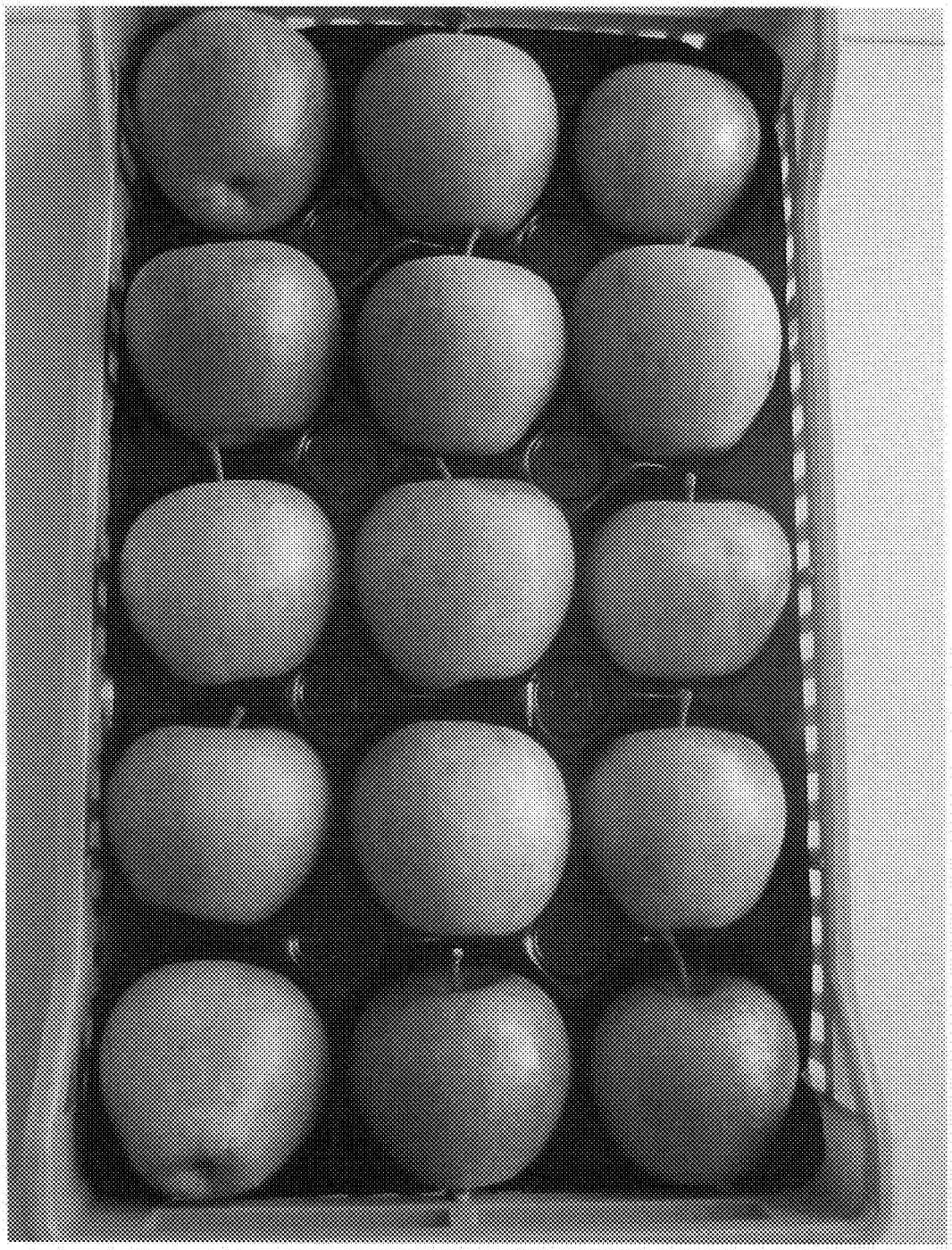

Latin name: *Malus domestica* Borkh.
Variety denomination: 'Daligris'.

CROSS REFERENCE TO RELATED APPLICATIONS

None.

PRIORITY CLAIM

None.

STATEMENT REGARDING FEDERALLY SPONSORED RESEARCH OR DEVELOPMENT

None.

BACKGROUND OF THE VARIETY

'Daligris' is a new and distinct cultivar of apple tree *Malus domestica* Borkh. 'Daligris' is a whole tree mutation of the apple variety 'Pinova' (U.S. Plant Pat. No. 11,601). The original whole tree mutation was discovered during the 1998 harvest in a commercial block of 'Pinova' trees near Lezigne-France, planted on M9 rootstocks in 1997. It was first asexually propagated in March 2000 for testing purposes by grafting under the breeder's reference number DDR14-51 at Doue la Fontaine, France. 'Daligris' was propagated for further experimentation in 2002.

The asexually propagated progeny of 'Daligris' has consistently been found to be homogeneous and stable, retaining the unique characteristics of the original 'Daligris' tree and fruit, and has remained true to type over successive asexually propagated generations. Plant Variety Rights have been applied for 'Daligris' in the European Union in 2006 under the application number 2006/1697.

BRIEF DESCRIPTION OF THE VARIETY

Trees of 'Daligris' have been virus tested, and have been found to be free from the most common apple viruses in Europe (stem pitting, stem grooving, rubbery wood, proliferation, spy decline, chlorotic leaf spot, russet ring, star crack, russet wart, mosaic). Virus free certified material will be available in 2009.

'Daligris' is quite similar to 'Pinova' with respect to tree behavior, flowers, and leaves. However, the fruit of 'Daligris' is notably distinct from 'Pinova,' and from 'Dalinip' (U.S. Plant Pat. No. 18,482), 'Dalirail' (U.S. Plant Pat. No. 18,483), and ROHO 3615(U.S. Plant Pat. No. 17,672), each of which is also a mutation of 'Pinova'.

TABLE 1

Comparison of 'Daligris' to 'Pinova' and Related Varieties (measurements given are approximate)

| Characteristic of the fruit | Pinova | Daligris | Dalinip | Dalirail | ROHO 3615 |
|---|---|---|---|---|---|
| Maturity | Third week of September | Fourth week of September | First week of September | Second week of September | Third week of September |
| Amount of russeting | Absent to very small | Typical light brown-yellow russeting on 25% to 40% of the skin surface | Absent to very small | Absent to very small | Absent to very small |
| Type of fore-ground Colour | Red 41A | Red 41A to Red-Orange 42A | Red 44A to Red-Orange 42A | Red 44A | Intense red 46A-46B |
| Amount of fore-ground Colour | 25-50% | 10-40% | 60-80% | 50-75% | 60-90% |
| Sugar content Average on 20 fruits from comparable trees | High: 13.4° brix | Very high: 15.5° brix | Similar to Pinova (around 13° brix) | Similar to Pinova (around 13° brix) | Similar to Pinova (around 13° brix) |

TABLE 1-continued

Comparison of 'Daligris' to 'Pinova' and Related Varieties (measurements given are approximate)

| Characteristic of the fruit | Pinova | Daligris | Dalinip | Dalirail | ROHO 3615 |
|---|---|---|---|---|---|
| Taste | Balanced in sugar and acidity with medium aroma | Pronounced aniseed flavor | Balanced in sugar and acidity with medium aroma | Balanced in sugar and acidity with medium aroma | Balanced in sugar and acidity with medium aroma |

TABLE 1-continued

Comparison of 'Daligris' to 'Pinova' and Related Varieties (measurements given are approximate)

| Characteristic of the fruit | Pinova | Daligris | Dalinip | Dalirail | ROHO 3615 |
|---|---|---|---|---|---|
| Size of Lenticels | Small (average: 0.5 mm) | Very large and very prominent (average: 1.2 mm) | Small (average: 0.5 mm) | Small (average: 0.5 mm) | Small (average: 0.5 mm) |

The Tree

The tree of 'Daligris' is a bit more dwarf than 'Pinova'. The branches, leaves and flowers of 'Daligris' are similar to 'Pinova'. The bloom is also similar to 'Pinova' in terms of bloom date range and intensity. Like its parent 'Pinova', 'Daligris' is very precocious and does not tend to alternate bearing. Productivity is comparable to 'Pinova'.

The Fruit

'Daligris' is very similar to 'Pinova' in term of fruit shape and size. Harvest of 'Daligris' has been observed to begin approximately one week later than 'Pinova'. The storageability of 'Daligris' is very similar to 'Pinova'.

The fruit of 'Daligris' is very distinctive from 'Pinova' in appearance:

- it is partially covered with a smooth light brown to yellow russeting which fully covers the stem cavity and then spreads out on the cheeks of the fruit;
- the lenticels are much larger and much more prominent than on 'Pinova'. They are russeted and bumpy; and
- 'Daligris' has a typical red-orange over-color, as distinguished from the red-pink over-color of 'Pinova'.
- 'Daligris' also has a consistent distinctive eating quality:
- Quantitative analyses (as presented in the table below) show that 'Daligris' consistently has a higher sugar content than 'Pinova'; and
- 'Daligris' has a pronounced aniseed flavor which, combined with the high sugar level, gives a unique taste to the variety.

TABLE 2

Comparison of 'Daligris' to 'Pinova' (measurements given are approximate) (Average of 20 fruits observed in comparative trials between 'Daligris' and 'Pinova' trees on M9 rootstock, similar crop load, same age)

| Year | 2005 | | 2006 | | 2007 | | 2008 | |
|---|---|---|---|---|---|---|---|---|
| Variety | Pinova | Daligris | Pinova | Daligris | Pinova | Daligris | Pinova | Daligris |
| % Russet | 2 | 26 | 4 | 32 | 10 | 41 | 4 | 39 |
| % Over-color | 23 | 19 | 25 | 27 | 21 | 30 | 35 | 28 |
| Sugar (° brix) | 12 | 14.5 | 13.2 | 14.2 | 14.3 | 17.1 | 13.4 | 15.5 |
| Starch 6.4 test | 7.1 | 6.6 | 7.0 | 8 | 7.2 | 7.3 | 5.9 | |
| Harvest Date | Sept 19th | Sept 29th | Sept 14th | Sept 19th | Sept 20th | Sept 28th | Sept 22nd | Sept 29th |

BRIEF DESCRIPTION OF THE PHOTOGRAPHS

Figure 2:
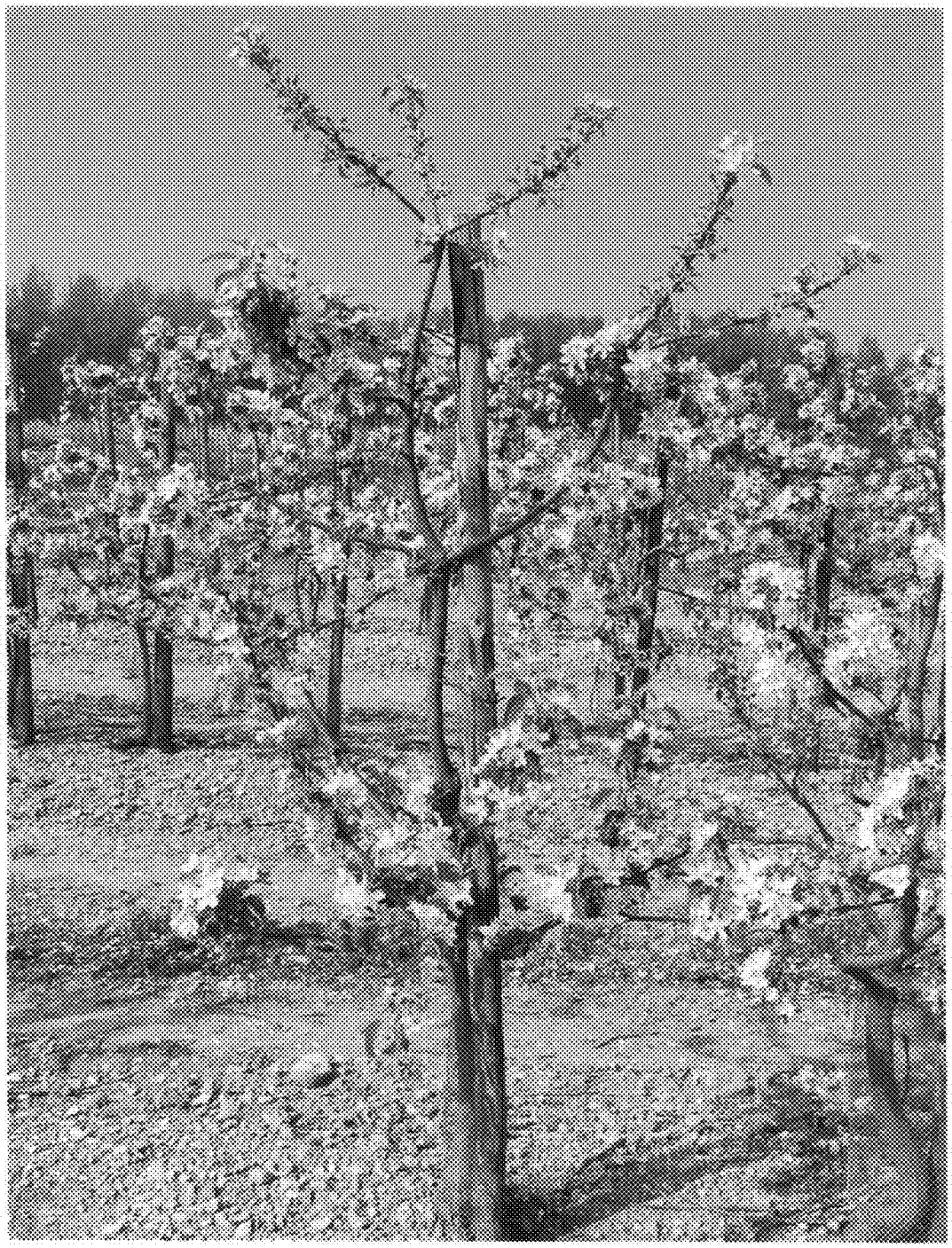
Figure 3:
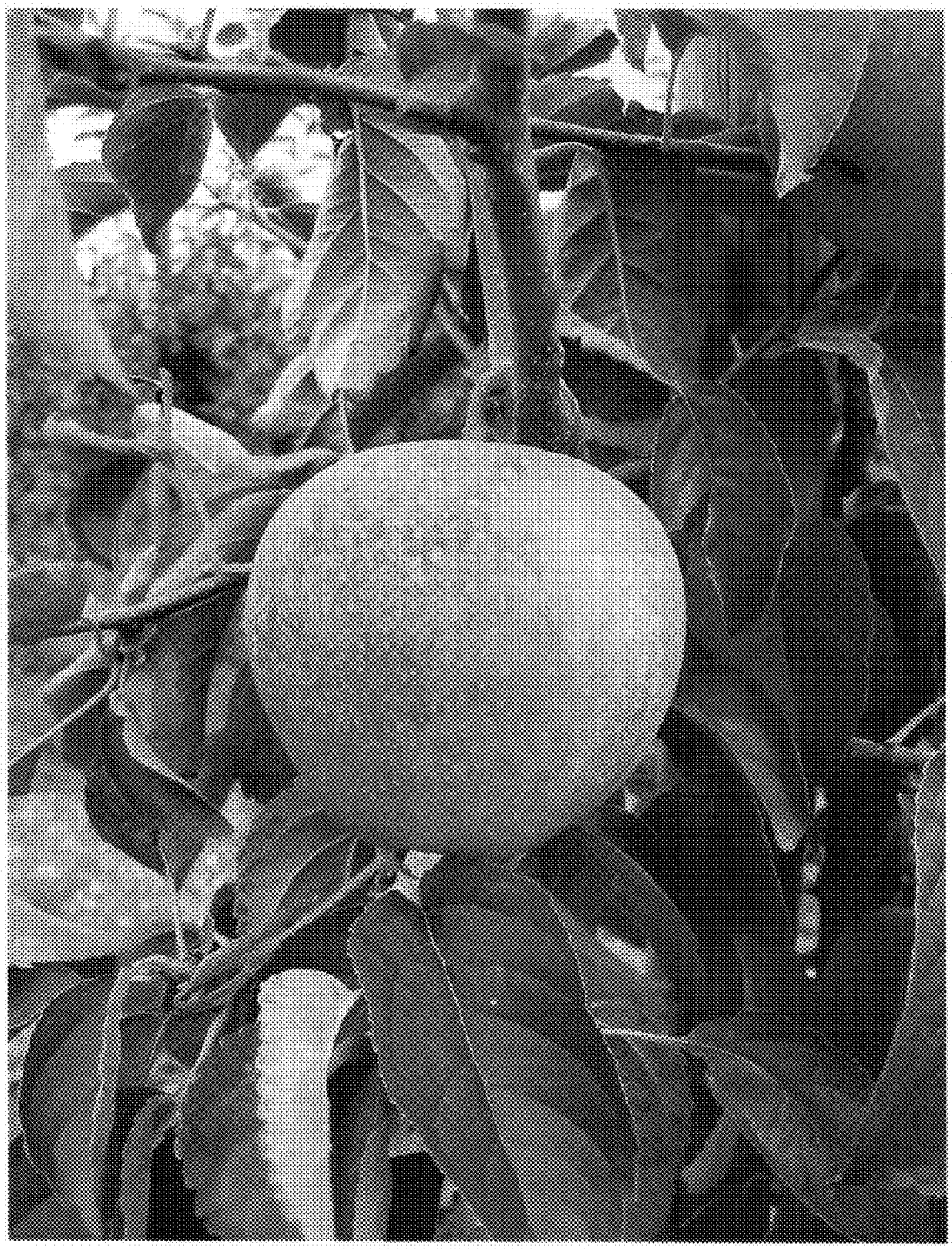
Figure 4:
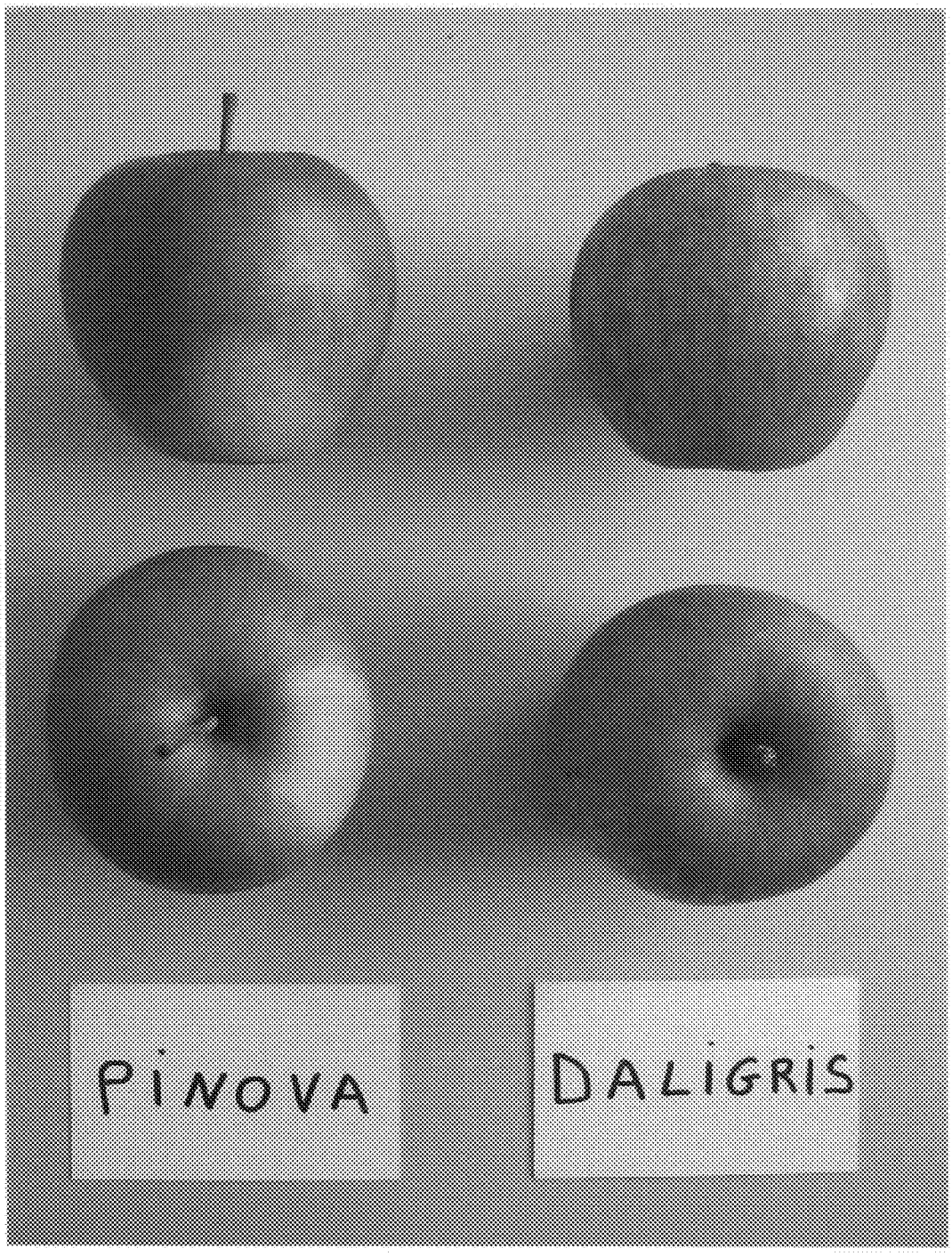

FIG. 1 shows the fruit of 'Daligris' after harvest;
FIG. 2 shows 'Daligris' in bloom in an orchard;
FIG. 3 shows 'Daligris' fruit on the tree; and
FIG. 4 shows 'Daligris' fruit as compared to 'Pinova' fruit.

DETAILED BOTANICAL DESCRIPTION OF THE VARIETY

The following detailed botanical description is based on general observations made of the mother tree from 1998 to 2003 and on second and third generation trees from 2002 to 2008. Quantified measurements of the trees, flowers and leaves are based on observations of three year old trees grown on M9 rootstock in a high density planting in the temperate climate of the Loire Valley, France. All colors are described according to The Royal Horticultural Society Colour Chart. It should be understood that the characteristics described will vary somewhat depending upon cultural practices and climatic conditions, and will vary with location and season. The measurements of any individual plant, or any group of plants, of the new variety may vary from the stated average.

Tree:

*Vigor.*—Weak to medium (less than 'Pinova').
*Type.*—Spur to ramified (a little less ramified than 'Pinova').
*Habit.*—Upright.
*Height.*—Low to medium (191 cm).

*Diameter.*—Medium (101 cm).
*Trunk diameter* (*at* 30 *cm above the graft union*).—Medium (35 mm).
*Bark texture.*—Smooth to medium.
*Bark coloration.*—Grey 201C.

Branch (fruiting branches located at around 1 m above the graft union):
*Length.*—Short to medium (avg. 41 cm).
*Diameter.*—Medium (avg. 19 mm).
*Crotch angle.*—60° to 80°.
*Bark color.*—Brown 200B.

One year old shoot:
*Length.*—Medium (avg. 16.3 cm).
*Color.*—Brown 200B.
*Pubescence* (*on upper half of the shoot*).—Medium.
*Thickness.*—Medium thick (avg. 6.4 mm).
*Internode length.*—Short (avg. 10 mm).
*Number of lenticels.*—Medium (6 lenticels per $cm^2$).

Winter hardiness:
*Hardiness.*—Similar to 'Pinova'.
*Chilling requirement.*—Similar to 'Pinova'.

Flower buds:
*Quantity per spur.*—2 to 3.
*Shape.*—Conical.
*Length.*—Medium (avg. 12 mm).
*Diameter.*—Medium (avg. 8 mm).
*Color.*—Red purple 61A.

Flowers:
*Color* (*balloon stage*).—Purple 77C.
*Diameter of open flower.*—Large (avg. 3.6 cm).
*Relative position of petal margin.*—Not touching.
*Number per cluster.*—5 to 7.

Bloom date:
*Date of first bloom.*—April 15 in Angers, France (comparable to 'Pinova').
*Date of full bloom.*—April 20 in Angers, France (comparable to 'Pinova').

Petals:
*Number per flower.*—5.
*Shape.*—Oval.
*Length.*—Medium long (avg. 20 mm).
*Width.*—Medium wide (avg. 15 mm).
*Apex.*—Round.
*Base.*—Pointed.
*Margin.*—Smooth.
*Coloration of upper surface.*—White 155B with purple 76B included herein.
*Coloration of lower surface.*—Purple 77D.

Pistils:
*Size.*—Long (13 mm).
*Color.*—Yellow green 145D.

Anthers:
*Quantity.*—Numerous (avg. 17 per flower).
*Size.*—Medium (avg. 2 mm).
*Presence of pollen.*—Present.
*Color of pollen.*—Yellow 4C.

Stigma:
*Size.*—Small to medium (avg. 0.5 mm).
*Color.*—Pale yellow 9C.

Style:
*Size.*—Medium to long (avg. 9 mm).
*Color.*—Yellow green N144D.

Ovary:
*Size.*—Medium (avg. 2 mm).
*Color.*—Green 134B.

Pedicel:
*Length.*—Medium (avg. 2 cm).
*Diameter.*—Thin (avg. 1.4 mm).
*Color.*—Green 142C.

Sepals:
*Quantity.*—5.
*Coloration.*—Green 143C.
*Shape.*—Conical pointed.

Leaves:
*Shape.*—Oblanceolate.
*Length* (*petiole not included*).—Long (avg. 11.1 cm).
*Width.*—Medium-wide (avg. 5.9 cm).
*Length/width ratio.*—Medium (2).
*Blade margin.*—Crenate.
*Apex.*—Acuminate.
*Base shape.*—Oblique.
*Color of upper surface.*—Green 143A (in early summer).
*Color of lower surface.*—Green 143C (in early summer).
*Attitude in relation to shoot.*—Upward.

Petiole:
*Length.*—Long (avg. 3.5 cm).
*Diameter.*—Thick (avg. 1.6 mm).
*Coloration.*—Yellow green 145B.

Fruit:
*Quantity per cluster.*—3 to 4.
*Size.*—Medium large (avg. 71 mm).
*Weight.*—Medium (avg. 166 g).
*Ratio of height to width.*—Small to medium (0.9).
*General shape in profile.*—Conical to truncate conical.
*Position of maximum diameter.*—Top third of the fruit.
*Ribbing.*—Absent.
*Aperture of eye.*—Closed.
*Size of eye.*—Large (avg. 9.5 mm).
*Length of sepal.*—Long (avg. 7.7 mm).
*Depth of eye basin.*—Deep (avg. 11.5 mm).
*Width of eye basin.*—Medium (avg. 29 mm).
*Length of stalk.*—Medium long (avg. 29 cm).
*Thickness of stalk.*—Medium (avg. 2.1 mm).
*Width of stalk cavity.*—Medium (avg. 33 mm).
*Depth of stalk cavity.*—Flat (avg. 7 mm).
*Size of lenticels.*—Very large (avg. 1.2 mm).
*Number of lenticels.*—Medium.
*Bloom of skin.*—Absent or very weak.
*Greasiness of skin.*—Weak to moderate.
*Background color of skin.*—Yellow 13C.
*Amount of over color.*—Low (10% to 40%).
*Over color of skin.*—Red stripes 41A on red orange 42A.
*Intensity of over color.*—Light to medium.
*Amount of russet around stalk cavity.*—Very high.
*Amount of russet on cheeks.*—Medium to high.
*Area of russet around eye basin.*—Low.
*Relative area of fruit covered with russeting.*—Medium to high (20% to 40%).
*Flesh texture.*—Firm.
*Aroma.*—Very intense.
*Flavor.*—Sweet with an aniseed flavor.
*Juiciness.*—Medium.
*Brix.*—Very high (2° brix higher than 'Pinova').
*Flesh coloration.*—Yellow 11D.
*Stem coloration.*—Grey brown N199D.

Seeds:

*Quantity per fruit.*—5 on average.

*Shape.*—Truncate ovoid.

*Coloration.*—Brown 200D.

Harvest:

*Beginning of harvest.*—Last week of September (1 week after the beginning of 'Pinova's' harvest).

*Harvest window.*—3 weeks.

*Number of picks.*—Three picks.

*Amount of fruit produced per tree per harvest.*—60 fruits on third leaf tree.

*Time for eating maturity.*—Late.

I claim:

1. A new and distinct apple tree substantially as described and illustrated herein.

* * * * *